United States Patent [19]
Miles

[11] Patent Number: 5,913,830
[45] Date of Patent: Jun. 22, 1999

[54] RESPIRATORY INDUCTIVE PLETHYSMOGRAPHY SENSOR

[75] Inventor: Laughton E. M. Miles, Los Altos Hills, Calif.

[73] Assignee: Respironics, Inc., Pittsburgh, Pa.

[21] Appl. No.: 08/915,210

[22] Filed: Aug. 20, 1997

[51] Int. Cl.⁶ ........................................ A61N 5/00
[52] U.S. Cl. .................... 600/535; 600/534; 324/207.16; 324/207.22
[58] Field of Search ...................... 600/534–535; 324/207.16, 207.22

[56] References Cited

U.S. PATENT DOCUMENTS

| | | |
|---|---|---|
| 3,560,845 | 2/1971 | Goldberg et al. . |
| 4,308,872 | 1/1982 | Watson et al. . |
| 4,373,534 | 2/1983 | Watson . |
| 4,817,625 | 4/1989 | Miles . |
| 5,611,349 | 3/1997 | Halleck et al. . |

FOREIGN PATENT DOCUMENTS 2116725  9/1983  United Kingdom ................... 128/721

OTHER PUBLICATIONS

Milledge, J.S., and Stott, F.D., "Inductive Plethysmography—a New Respiratory Transducer", Proceedings of the Physiological Society, Jan. 1977, pp. 4–5.

Shapiro, A. and Cohen, H.D. (1965) "Transactions of the New York Academy of Science", vol. 27, p. 634.

Konno, K. and Mead, J. (1967) "Journal of Applied Physiology", vol. 22, p. 407.

Primary Examiner—Robert L. Nasser
Assistant Examiner—Michael Astorino
Attorney, Agent, or Firm—Reed Smith Shaw & McClay LLP

[57] ABSTRACT

An improved inductive plethysmography sensor involving a conductor having alternating active and inactive segments. The active segments preferably have a narrow diamond shape which minimizes the possibility of artifact. Because of the conductor design, the sensors can be placed completely about the chest and abdomen with any overlap arranged so that active segments overlap inactive segments.

19 Claims, 2 Drawing Sheets

RESPIRATORY INDUCTIVE PLETHYSMOGRAPHY SENSOR

FIELD OF INVENTION

The present invention relates to an improved inductive plethysmography respiration sensor for measuring the change of circumference and cross-sectional area of the chest or abdomen, and thus respiration volume.

BACKGROUND OF THE INVENTION

The field of plethysmography, the study of the change in size of an organ or limb, often employs inductive sensors as measuring devices. A variety of such sensors have been disclosed in various patents to Goldberg et al., including U.S. Pat. No. 3,560,845. The use of such a sensor to measure cross-sectional area changes in the torso, and thus respiration volume has been discussed in Milledge, J. S., and Stott, F. D., "Inductive Plethysmography—A new Respiratory Transducer", *Proceedings of the Physiological Society*, January 1997, pages 4–5. By measuring the simultaneous changes in airflow, the changes in the signals from various types of chest and abdominal respiration sensors can be weighted and summed in order to provide an independent measurement of respiration volume. Such calibration procedures were described by Shapiro, A. and Cohen, H. D. (1965) "Transactions of the New York Academy of Science", Vol. 27, page 634. Such techniques were further explored in Konno, K. and Mead, J. (1967) "Journal of Applied Physiology", Vol. 22, page 407. In U.S. Pat. Nos. 4,308,872 and 4,373,534, Watson et al. further describe the use of inductive phethysmography sensors which measure cross-sectional area.

The use of an inductive sensor which circumscribes the torso has been found to have certain inherent disadvantages. Non-invasive respiration inductive sensors are usually only semiquantitative and subject to artifact due to body movement, changes in sleeping position, physical displacement, physical deformation, changes in relative calibration of the chest and abdominal compartments, electrical interference by the chest sensor to the abdominal sensor (and vice-versa), and electrical interference from external electromagnetic fields including electrical magnetic properties of the torso.

An improved self-inductance sensor is disclosed in U.S. Pat. No. 4,817,625 to Miles (the inventor of the present invention), the disclosure of which is incorporated by reference. This improved sensor includes a band of distensible material and a strap of nondistensible material. The band and strap in combination form a closed loop which circumscribes the object to be measured. A conductor is secured to the band and has two symmetric portions each having a saw-toothed configuration and juxtaposed to one another. The respective portions of the conductor form a plurality of substantially enclosed diamond shaped areas. The change in shape of the areas results in a change in the self-inductance of the conductor. While the sensor of the '625 patent overcomes several of the drawbacks associated with prior sensors, some disadvantages have been found when the upper and lower angle of the enclosed diamond shaped area approaches 90°. When the upper and lower angles are less than 90°, inductance decreases when the belt is stretched. When the upper and lower angles are greater than 90°, inductance increases when the belt is stretched. However, when the upper and lower angles are stretched or compressed such that they pass through an angle of 90°, the signal will reverse and disrupt operation of the sensor. Thus, an advantage exists for maintaining the upper and lower angles either at an angle greater than 90° or less than 90° at all times to ensure efficient operation.

The inductance measurement area of the sensor of the '625 patent does not encompass the entire torso as the conductor does not run through the strap of nondistensible material. Thus, the accuracy of the sensor is dependent on the position of the patient. Thus, an advantage exists for a self-inductance sensor in which the conductor portion entirely circumscribes the object to be measured.

An advantage would also exist for an improved inductive plethysmography respiration sensor which is less sensitive to changes in sleeping position, less sensitive to movement artifact and more sensitive to small changes in chest or abdominal circumference.

SUMMARY OF THE INVENTION

The present invention provides an improved inductive plethysmography sensor which involves a new shape for the conductor having first and second portions, (a) the sensor contains alternating active and inactive segments, and (b) the active segment preferably has a narrow diamond shape which minimizes the possibility of artifact. The upper and lower angles of the diamond can either be acute or obtuse (i.e. the upper angle is formed solely by the first portion, and the lower angle is formed solely by the second portion). Because of the improved design, the sensors can be placed completely about the chest and abdomen with any overlap arranged so that active segments overlap inactive segments. By altering the length of the straight segments, or by angling the straight segments, the sensors can be of varying total lengths without altering the electrical properties of the sensor. Although the presently preferred embodiment of the present invention includes insulated wire attached to a fabric belt, other arrangements are possible. In one such alternate embodiment described herein individual swatches of an elastic transparent urethane film or the like are attached to individual diamond-shaped active segments while no backing is attached to the straight segments. An adhesive is used to attach the swatches to the body. This allows the straight segments to be angled for a wide variety of arrangements about the body. In another alternate embodiment conductive material, i.e. aluminum paper, is embedded in commercially available medical adhesive plastic foam.

The inductive plethysmography respiration sensor of the present invention demonstrates many advantages over prior inductive plethysmography sensors. The sensor of the present invention is less likely to be effected by movement or positional artifact and electrical interference. Sensors of different lengths can be used on patients of different ages and sizes. The present sensor is more sensitive to changes in chest or abdominal circumference and less likely to become displaced from the intended position. The function of the sensor is further improved by attaching it to the skin with an adhesive.

By calibrating the signals measured by the present invention against the signals from a device measuring absolute respiratory tidal volume, it should be possible to use the new sensor to obtain a continuous non-invasive measurement of tidal volume in different sleeping positions and different relative amounts of chest and abdominal breathing, and to be able to see more detail in the calculated flow signals, including but not limited to evidence of upper airway flow limitation.

The invention will become more readily apparent from the following description of a preferred embodiment of the invention thereof shown, by way of example in the accompanying drawings. It is to be expressly understood, however, that the drawings are for the purpose of illustration and description only and are not intended as a definition of the limits of the invention.

DESCRIPTION OF THE INVENTION

Figure 1:
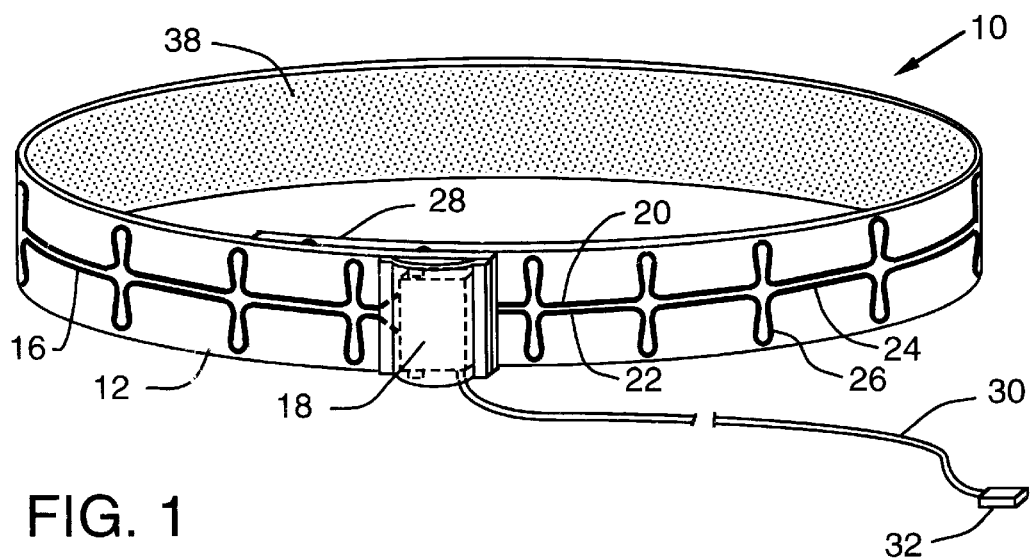
FIG. 1. is a perspective view of a presently preferred embodiment of the sensor of the present invention.
Figure 2:
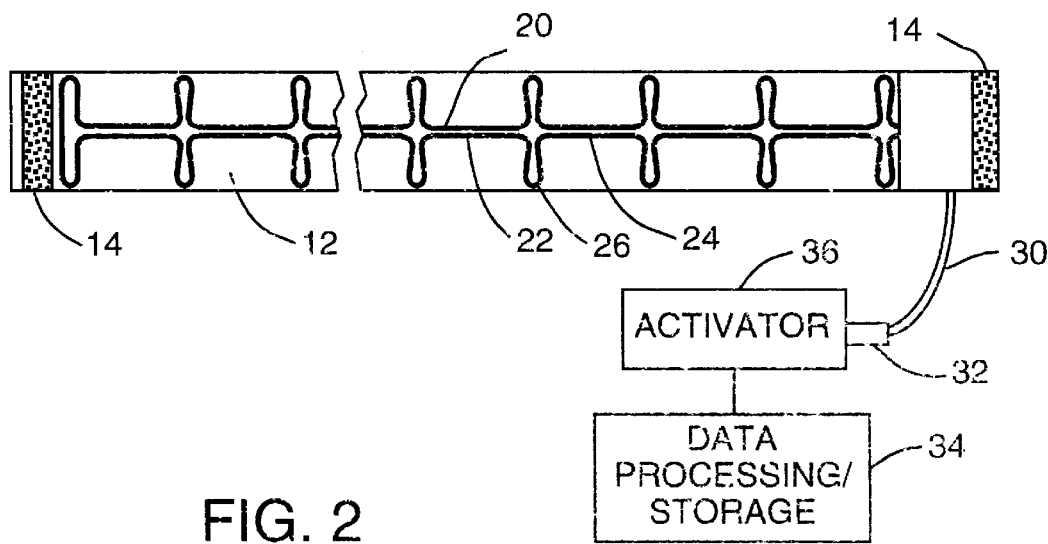
FIG. 2 is a plan view of the presently preferred embodiment of FIG. 1.

A preferred embodiment of the inductive plethysmography sensor 10 of the present invention is illustrated by way of reference to FIGS. 1 and 2. The sensor includes a band 12 of distensible material, typically a Lycra type or rubber material. The distensible band 12 includes several complimentary areas of hook and loop fasteners 14 so that the band can be adjusted to fit around a variety of patients.

A conductor 16 is attached to the distensible band. A transformer 18 is preferably attached near one end of the band by folding one end of the band over the transformer and attaching with hook and loop fasteners. The conductor 16 comprises a loop emanating from the transformer to the other end of the band and back again. The conductor 16 includes two symmetric portions 20, 22 forming alternating parallel straight 24 and narrow diamond-shaped segments 26. In this preferred embodiment, the narrow diamond-shaped segment's have acute upper and lower angles forming oppositely projecting nodes or spikes.

The straight segments 24 are inactive segments and the narrow diamond-shaped segments 26 are active segments. When the band 12 is completely placed around the chest, any overlap 28 is arranged so that active segments 26 overlap inactive segments 24. The narrow diamond-shaped segments 26 of the conductor 16 form a plurality of substantially enclosed areas. It should be recognized that a variety of arrangements are possible for forming a series of active and inactive segments. The change in shape of the areas results in a change in the self-inductance of the conductor.

The transformer 18 is preferably of the type described in more detail in U.S. Patent No. 4,817,625 having primary and secondary coils (not illustrated). A cable 30 is attached at one end to the transformer 18. A connector 32 at the distal end of the cable 30 attaches the sensor 10 to a data processor storage device 34 and activating circuitry 36 which provides the alternating current used to excite the primary coil. The alternating current from circuitry is passed through cable 30 to induce a corresponding current in conductor. The phase shift in the current in cable 30 as it passes through the secondary coil is indicative of the self-inductance of the activated conductor 16.

In operation, sensor 10 is employed in respiration plethysmography by locating a pair of sensors 10 about the chest and abdomen of the patient, and fixing the sensors 10 to the patient with the hook and loop fasteners 14. The sensors 10 are placed about the patient such that the conductor 16 is on the side away from the body. If necessary, the ends of the band are overlapped 28 such that active segments 26 overlap inactive segments 24. The function of the sensor 10 can be further improved by applying an adhesive 38 to the patient side of the belt such as a typical urethane based biomedical adhesive spray before attaching to the patient. As the patient breathes the distensible band 12 expands and contracts. An alternating current from the transformer 18 flows through the conductor 16. The self-inductance in the conductor 16 caused by the alternating current changes as the band distends and the areas 26 change shape. This change in inductance is sensed through the transformer 18, typically in the form of a change in the frequency of the induced alternating current, or in the form of a change in the phase or phase-shift network. The connector 32 is attached to activating circuitry 36 which is in turn connected to a data processing device or data recorder 34 which weights, sums and calibrates the data from chest and abdominal sensors to derive respiration volume.

Figure 3:
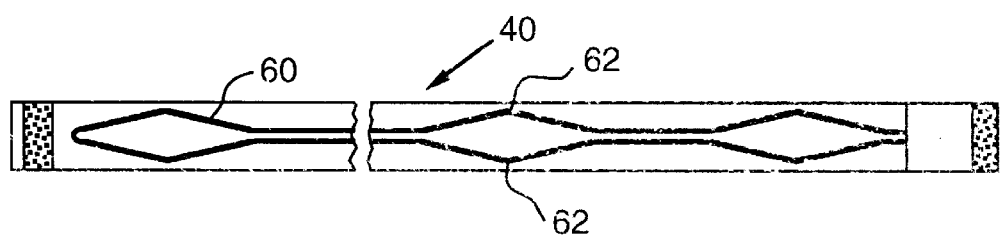
FIG. 3 is a plan view of a second embodiment of the present invention.

In a second embodiment 40 illustrated in FIG. 3, the narrow diamond-shaped areas 60 have upper and lower angles 62 which are obtuse. This allows the band 12 to be much narrower which is an advantage when using the sensor with infants.

Figure 4:
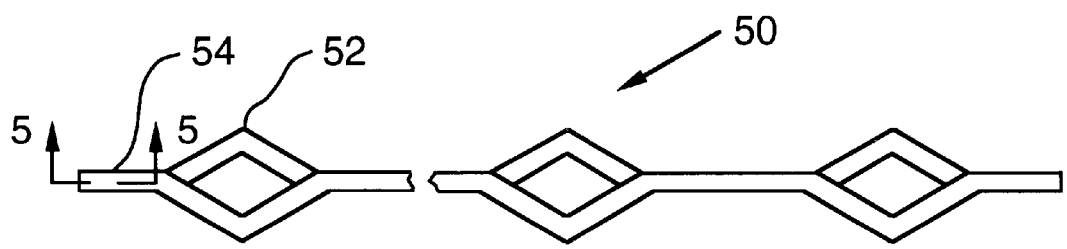
FIG. 4 is a plan view of a third embodiment of the present invention.
Figure 5:
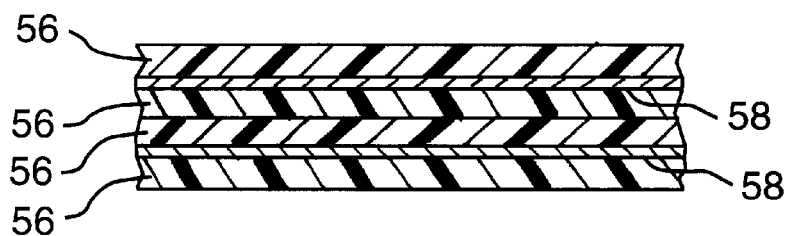
FIG. 5 is a partial cross-sectional view of the third embodiment.

In a third embodiment 50 illustrated in FIG. 4, conductive material is embedded in commercially available medical adhesive plastic foam. The upper and lower angles of narrow-diamond shaped areas may have acute angles or obtuse angles 52 (as shown in this Figure). The two symmetric portions of the conductor in the parallel inactive segments 54 may lie on top of each other such that the inactive segments comprise alternating layers of foam 56 and conductive material 58 (FIG. 5).

Figure 6:
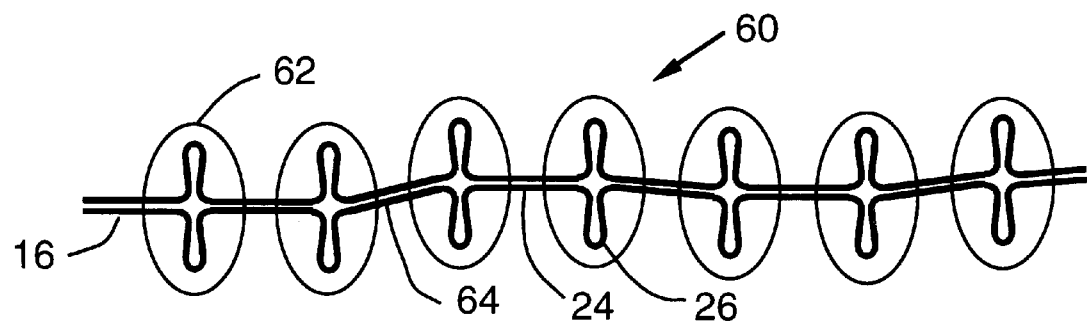
FIG. 6 is a plan view of fourth embodiment of the present invention in which the straight segments can be angled.

In a fourth embodiment 60 illustrated in FIG. 6, the distensible belt of the embodiment illustrated in FIGS. 1 and 2 is replaced with individual swatches 62 of distensible material attached to each diamond-shaped active segment. The individual distensible swatches may be coated with an adhesive (not illustrated in FIG. 6) to attach the distensible swatches 62 directly to the patient's skin. The straight inactive segments 64 do not have any backing. This allows the sensor to take on a variety of arrangements by angling 44 some or all of the straight inactive segments 24.

Although the invention has been described in detail for the purposes of illustration, it is to be understood that such detail is solely for that purpose and that variations can be made therein by those skilled in the art. In particular, while the invention has been described in terms of a respiration sensor, it is apparent that the sensor could be used in measuring the variable circumference of a wide variety of objects. It is to be understood that such modifications and adaptations are within the spirit and scope of the invention except as it may be limited by the scope of the following claims:

What is claimed is:

1. A self-inductance sensor for measuring the change in circumference of an object comprising:

an electrical conductor having a first portion and a second portion, each portion of the conductor closely juxtaposed to the other portion forming a repetitive pattern of alternating active segments and inactive segments, said active segments forming substantially enclosed areas being bounded by said first portion and by said second portion, said enclosed areas changing shape when said conductor is distended, said conductor being adapted to circumscribe the object; and means for measuring the self-inductance of the conductor to indicate the relative change in shape of the enclosed areas and, thus, the change in circumference of the object.

2. The sensor of claim 1, wherein the enclosed areas have upper and lower acute angles respectively formed by the first and second portions.

3. The sensor of claim 1, wherein the enclosed areas have upper and lower obtuse angles respectively formed by the first and second portions.

4. The sensor of claim 1, wherein the inactive segments are substantially straight and formed from parallel segments of the first and second portions.

5. The sensor of claim 1, further comprising individual swatches of distensible material attached to individual active segments for attaching the conductor to the object.

6. The sensor of claim 5, further comprising an adhesive applied to the individual swatches for attaching the conductor to the object.

7. The sensor of claim 1, further comprising an elongate band of distensible material to which the conductor is attached.

8. The sensor of claim 7, further comprising an adhesive applied to the band for attaching the conductor to the object.

9. The sensor of claim 1, wherein the measuring means includes means for measuring the phase shift in an alternating current applied to the conductor.

10. The sensor of claim 1, further comprising means for overlapping inactive and active segments.

11. The sensor of claim 1, wherein the conductor comprises a conductive material embedded in adhesive foam.

12. The sensor of claim 11, wherein the inactive segments comprise parallel superimposed segments of the first and second portions.

13. A self-inductance sensor for measuring the change in circumference of an object comprising:

an elongate band of distensible material adapted to circumscribe the object;

an electrical conductor secured to a first side the band and having a first portion extending from a first position adjacent one end of the band to a second position adjacent the other end of the band and a second portion extending from said second position to said first position, each portion of the conductor closely juxtaposed to the other portion forming a repetitive pattern of alternating active segments and inactive segments, said active segments forming substantially enclosed areas being bounded by said first portion and by said second portion, said enclosed areas changing shape when said band is distended; and means for measuring the self-inductance of the conductor to indicate the relative extension of the band and thus, the change in circumference of the object.

14. The sensor of claim 13, wherein the inactive segments are substantially straight and formed from parallel segments of the first and second portions.

15. The sensor of claim 13, further comprising means for adjustably securing the ends of the band together such that they overlap.

16. The sensor of claim 14, wherein said means for adjustably securing further comprises means for overlapping active segments and inactive segments when the ends of the band are secured.

17. The sensor of claim 15, further comprising an adhesive applied to a second side of the band opposite the first side.

18. The sensor of claim 13, wherein the enclosed areas have upper and lower acute angles respectively formed by the first and second portions.

19. The sensor of claim 13, wherein the enclosed areas have upper and lower obtuse angles respectively formed by the first and second portions.

* * * * *